(12) United States Patent
Medasani et al.

(10) Patent No.: US 9,603,885 B2
(45) Date of Patent: Mar. 28, 2017

(54) PICRORHIZA EXTRACT FOR PREVENTION, ELIMINATION AND TREATMENT OF INFECTION DISEASES

(71) Applicant: MUNISEKHAR MEDASANI, Hyderabad (IN)

(72) Inventors: Munisekhar Medasani, Hyderabad (IN); Satyasayee Divi, Vishakapatnam (IN)

(73) Assignee: Munisekhar Medasani, Hyderabad (IN)

( * ) Notice: Subject to any disclaimer, the term of this patent is extended or adjusted under 35 U.S.C. 154(b) by 0 days.

(21) Appl. No.: 14/846,249

(22) Filed: Sep. 4, 2015

(65) Prior Publication Data

US 2015/0374774 A1    Dec. 31, 2015

Related U.S. Application Data

(62) Division of application No. 13/391,524, filed as application No. PCT/IN2010/000584 on Sep. 2, 2010, now Pat. No. 9,125,921.

(30) Foreign Application Priority Data

Sep. 4, 2009  (IN) .......................... 2150/CHE/2009

(51) Int. Cl.
| | |
|---|---|
| A61K 36/00 | (2006.01) |
| A61K 36/80 | (2006.01) |
| A61K 36/68 | (2006.01) |
| A61K 39/12 | (2006.01) |
| A61K 39/39 | (2006.01) |
| A23L 33/105 | (2016.01) |
| A23L 33/12 | (2016.01) |
| A61K 39/00 | (2006.01) |

(52) U.S. Cl.
CPC ............ *A61K 36/80* (2013.01); *A23L 33/105* (2016.08); *A23L 33/12* (2016.08); *A61K 36/68* (2013.01); *A61K 39/12* (2013.01); *A61K 39/39* (2013.01); *A23V 2002/00* (2013.01); *A61K 2039/55588* (2013.01)

(58) Field of Classification Search
None
See application file for complete search history.

(56) References Cited

U.S. PATENT DOCUMENTS

| 5,145,955 A | 9/1992 | Aswal et al. |
| 2008/0160042 A1 | 7/2008 | Olalde Rangel |

FOREIGN PATENT DOCUMENTS

| CN | 1594356 A | 3/2005 |
| CN | 101049366 A | 10/2007 |
| IN | 189316 A1 * | 2/2003 |
| IN | 20050151313 | 1/2006 |
| JP | 2006257060 A * | 9/2006 |
| RU | 2311194 C1 | 11/2007 |

OTHER PUBLICATIONS

Walker, Personality, coping and sex as psychosocial aspects of psoriatic arthropathy, Dermatology and Psychosomatics, (2003) vol. 4, No. 1, pp. 27-32.*
Yu et al, Effects of long-term oral administration of polymeric microcapsules containing tyrosinase on maintaining decreased systemic tyrosine levels in rats, Journal of pharmaceutical sciences, (Apr. 2004) vol. 93, No. 4, pp. 831-7.*
Cleaver, Defective repair replication of DNA in xeroderma pigmentosum, Nature [London], (1968) vol. 218, No. 5142, pp. 652-656.*
Jullien, A new treatment for psoriasis, Nouvelles Dermatologiques, (Apr. 2006) vol. 25, No. 4, pp. 264-272.*
Granger et al, Association between dietary fat and skin cancer in an Australian population using case-control and cohort study designs, BMC Cancer (2006), 6: 1-7.*
Skin disorders in Merck manual, accessed on Feb. 3, 2009, pp. 1-2.*
Vitiligo in Merck manual, accessed on Feb. 3, 2009, pp. 1-2.*
Khajuria et al., "RLJ-NE-299A: A New Plant Based Vaccine Adjuvant", Vaccine, 2007, pp. 2706-2715, vol. 25.
Thyagarajan et al., "Herbal Medicines for Liver Diseases in India", Journal of Gastroenterology and Hepatology, 2002, pp. S370-S376, vol. 17.
Vaidya et al., "Picrorhiza Kurroa (Kutaki) Royle Ex, Benth as a Hepatoprotective Agent—Experimental & Clinical Studies", J. Postgrad. Med., 1996, vol. 4, No. 42, pp. 105-108.
Anonymous, "Picrorhiza Kurroa", Alternative Medicine Review, 2001, pp. 319-321, vol. 6, No. 3.
Pandey et al., "Immunopharmacological Studies on Picrorhiza Kurroa Royle-ex-Benth, Part III: Adrenergic Mechanisms of Anti-Inflammatory Action", Indian Journal of Physiology and Pharmacology, 1988, vol. 32, No. 2, 1 page (<http://imsear.hellis.org/handle/123456789/107766>), abstract only.
Kamble et al., "Hepatoprotective Activity Studies of Herbal Formulations", International Journal of Green Pharmacy, 2008, pp. 147-151.

(Continued)

*Primary Examiner* — Qiuwen Mi
(74) *Attorney, Agent, or Firm* — Oliff PLC

(57) ABSTRACT

An anti-viral composition comprising terpenes and fatty acids found in the Scophulariaceae family of plants is disclosed. It further comprises other lipophillic constituents and the aglycons of the glycosides occurring in said family of plants. Preferably, the composition is derived by extraction of the roots and rhizomes of mixtures of *Picrorhiza kurrooa* Royle, *Picrorhiza scrophularflora* Pennell and *Neopicrorhiza scrophula iflora*. Solvents and solvent combinations are disclosed. The composition is effective against both DNA and RNA viruses and against fungal, bacterial, parasitic and protozoal infections and diseases and also as a hepatoprotective, anti-hyperlipidemic, anti-diabetic and kidney-protective agent. Anti-bodies and vaccines for the cited diseases can be made by administration of the composition to animal or other subjects.

28 Claims, No Drawings

(56) References Cited

OTHER PUBLICATIONS

Anonymous, "Picrorhiza Kurroa—Evaluation of Therapeutic Properties", Alternative Medicine Review, 2001 (4 pages) (http://findarticles.com/p/articles/mi_m0FDN/is_3_6/ai_76487135/).
Russo et al., "Indian Medicinal Plants as Antiradicals and DNA Cleavage Protectors", Phytomedicine, 2001, vol. 8, No. 2, pp. 125-132.
International Search Report for International Application No. PCT/IN2010/000584 mailed Apr. 29, 2011.
Written Opinion of the International Searching Authority for International Application No. PCT/IN2010/000584 mailed Apr. 29, 2011.
Neopicrohiza scrophulariflora from USDA, accessed on Aug. 12, 2013, pp. 1-3.
Rzadkowska-Bodalska et al, Chemical and biological investigation of lipophilic fraction of Linaria vulgaris Mill. (Scrophulariaceae), Bulletin of the Polish Academny of Sciences Biological Sciences, (1995 (1996)) vol. 43, No. 3-4, pp. 179-184.
Leider et al, Determination of the mutation rate of a retrovirus. Journal of virology, (Sep. 1988) Vo. 62, No. 9, pp. 3084-3091.
Del Rio, Report from the 15th Retrovirus Conference. More setbacks in HIV prevention. AIDS clinical care, (Apr. 2008) vol. 20, No. 4, pp. 25-26.
Sharp, 14th annual retrovirus conference (CROI), HIV prevention update. Some bad news, some good news. Positively aware the monthly journal of the Test Positive Aware Network, (May-Jun. 2007) vol. 18, No. 3, pp. 26-27.
Retrovirus from Wikipedia, accessed on Nov. 4, 2012, pp. 1-8.
Badary et al. Prospects for drug treatment of AIDS. Saudi Pharamaceutical Journal (1999), 7(3), 77-102.
Miyazawa et al. Volatile components from the roots of Scrophularia ningpoensis Hemsl. Flavour and Fragrance Journal (2003) vol. 18, No. 5, pp. 398-400.

\* cited by examiner

PICRORHIZA EXTRACT FOR PREVENTION, ELIMINATION AND TREATMENT OF INFECTION DISEASES

This application is a divisional application of U.S. patent application Ser. No. 13/391,524 filed Feb. 21, 2012, which is the U.S. national phase of International Application No. PCT/IN2010/000584, filed Sep. 2, 2010. The entire disclosures of these applications are incorporated herein by reference.

This invention relates to a medicinal, nutraceutical and food composition for use in the prevention, elimination, treatment and management of infections, disorders and diseases in human and animal subjects and in the biotech industry; to the use and the method of treatment thereof in the said prevention et al of infections, disorders and diseases caused by viruses, fungi, bacteria, parasites and protozoa microorganisms; to a process of making said composition by the extraction of the plant matter of the Scrophulariaceae family(order) of plants and to the said extract and the fractions thereof; and to a process for making said composition by the admixture of the constituents thereof.

The plants of the order Scrophulariaceae are known to possess medicinal properties as reported in traditional medicine systems. The medicinal efficacy of these plants arises from the numerous glycosides present in the plants of this order. The more accessible of Scrophulariaceae plants are the plants in the genus *Picrorrhiza*. Three members of this genus are of particular interest because of their safety and absence of toxicity. They are *Picrorhiza kurrooa* Royle, *Picrorhiza scrophulariflora* Pennell and *Neopicrorhiza scrophulariiflora*.

*Picrorhiza kurrooa* (known as Katuka in India) is widely found in India. It grows in the Himalayas at an altitude of about 3000 to 5000 metres. The extract is known for its properties as a liver protector and an immune modulator. Roots of the plant have been traditionally used in the Indian Ayurvedic system of medicine for asthma, bronchitis, malaria, chronic dysentery, viral hepatitis, upset stomach, scorpion stings, as a bitter tonic for stimulating the appetite and for improving digestion. It is known for its therapeutic value as a hepato-protectant and for relief in fevers but there is no disclosure or evidence in the prior art as to whether it acts against hepatitis or other viruses or is a mere liver rejuvenant.

The plant also grows in China, Nepal, Bhutan and other regions, where roots and rhizomes thereof have been traditionally used for dysentery, jaundice, steaming of bone, hepatoprotection and immuno-modulation function. The plant, particularly the roots, is known to be rich in terpenoids and glycosides.

The terms *Picrorhiza* and *Picrorrhiza*, with slightly different spellings are interchangeably used in this specification and are intended to be the same material. The species name *Picrorhiza kurrooa* is referred to hereinafter as *PK* for short in the interests of conciseness. In this specification, the initials '*PK*' refer to the said *Picrorhiza* species. Depending on the context, said initials may refer just one or the species or to more than one simultaneously. The initial '*P*' is used as an abbreviation for the term *Picrorhiza*. The terms 'principles' and 'factors' are also used interchangeably in this specification and are intended to mean the same unless otherwise required by the context.

References to 'extraction' in this specification may be to the process of extraction of the plant matter as a whole or to the individual operation of extraction which is one of the steps (the leaching or solid-liquid extraction step) in the said process. The meaning appropriate to the context may be taken. The terms 'component' and 'constituent' have been used interchangeably at some points herein, the meaning being quite clear from the context.

Plant matter refers to the starting material for the process of extraction of the invention the final product appearing at the end thereof being referred to as the extract. The term 'plant matter' has also been used to refer to the plant-matter-in-process that is, at different stages in the process. The liquid streams at various stages in the process are referred to either as the extracts or as the solution. The meaning appropriate to the context may be taken.

The active principle in *PK* is referred to in the prior art as kutkin which comprises kutkoside which is a glycoside. It further comprises iridoid glycosides named Picroside I, II, III and other picrosides. Several other principles have been identified such as apocynin, drosin and nine cucurbitacin glycosides, the first-named being a potent anti-inflammatory agent and the other two are also reported to have medicinal properties. These medicinal factors occur uniformly across the entire said order (the Scrophulariaceae family) and in particular in all the plants of the *P.* genus. Thus far, the said medicinal efficacy of *PK* extracts, has not been attributed to specific active principles (factors) in the prior art.

It is now known that plant matter of the *P.* genus in particular and the Scrophulariaceae family(S. family for short) in general comprise both lipophillic and non-lipophillic constituents. The lipophillic compounds and constituents of said family are referred to further herein as LCs for short and similarly the non-lipophillic constituents and compounds of the family as the NLCs. This is in the interests of conciseness and without any limitation to the scope of the invention.

Reference is made to the present applicant's co-pending application for patent No. 1917/CHE/2009 of $12^{th}$ Aug. 2009 relating to the extract of the said *P.* genus plants of the S. family.

These inventors observe that all the above named medicinal factors of *PK* that have been reported, discussed or investigated either in the traditional medicine practices or in the modern prior art are mainly NLCs. It may be noted that prior art (including traditional medicine practices) has confined itself to use of only water and alcohols (methanol and ethanol) as extracting solvents. These inventors note that said solvents generally speaking, extract the said NLCs, and almost leave out all the LCs. Consequently, the attention of the prior art has been solely on the NLCs and their medicinal properties and has not extended to these other components.

The chief NLC in *P.* plant matter are the glycosides thereof. In modern times, a wide range of medicinal properties of the various plant glycosides have come to light. They extend over a wide range of diseases and disorders. Different types of glycosides are found in the plant world. The focus and spotlight in the prior art, at least as far as medicinal properties and effects are concerned, has been totally on the *P.* glycosides. Prior art appears to be unaware of the nature and extent of the other constituents in the S. family of plants, namely the said LCs and their medicinal significance. This is understandable as the prior art has substantially excluded other solvents from their studies, solvents that would have extracted also the LCs to a greater or lesser extent and exposed them to research, study and medicinal scrutiny. Presumably, prior art would then have explored the nature and extent of their medicinal efficacies. Perhaps because the water and alcohol extracts exhibited considerable medicinal efficacy and offered enough scope for investigations, attention did not extend to the other extracting solvents and thereby to the lipophillic constituents of the S. family.

Through their experimental observations, these inventors have established that the medicinal activity of said LCs (lipophillic compounds of the S. family) is of a very high order. As first observed by these inventors the range and quantum of the medicinal effect of the said LCs in contrast to said glycosides is considerably and surprisingly higher and wider. This invention is the first to consider the said LCs and to verify their quite extraordinary medical significance, for example, as anti-viral compounds. This invention has also established for the first time that the presence of NLCs tends to impair and reduce the medicinal efficacy of the LCs and that it is therefore important to produce PK extracts that contain the LCs substantially exclusively or with the minimum of NLC content. To this end, these inventors provide a novel process and have identified appropriate solvents that preferentially extract said LCs and whose extraction profile is such as to substantially keep out said NLCs or minimise their extraction into the extract.

These inventors observe that the NLCs mask the medicinal effects of the LCs. The presence of any NLCs in an extract containing the said LCs has the effect of reducing the medicinal efficacy of the latter. It may be that some of the NLCs of the S. family have an action opposite to that of the LCs. Whatever the mechanism, this invention has experimentally established that the LCs have pronounced medicinal effects and that LC-extracts must be preferably substantially free of NLCs so as to realise their full medicinal efficacy.

The novel *PK* extract of the invention therefore differs in a very fundamental way from the *PK* extracts of prior art in that the medicinal principles in the former are different from that in the latter. The medicinal principles of the former are substantially absent in the latter and the medicinal principles in the latter have been substantially avoided in the former for reasons elaborated hereinbelow. The medicinal principles in the former are the LCs of the S. family of plants and not the S. family glycosides as is the case with the latter.

The chief medicinal factors in the former are the fatty acids and terpenes found in the S. family of plants followed by the aglycons arising from the S. family glycosides. Said fatty acids, terpenes and aglycons extracted out in the extract in the process are absent in the latter. As is known, the glycosides in *PK* plants are the picrosides I, II and III etc. The latter therefore consists mainly of said picrosides and a compound named apocynin while the former is substantially free of both said picrosides and other glycosides and also apocynin. Rather than the said picrosides present in the original plant matter, what we have in the extract of the invention are aglycons derived therefrom.

It may therefore be noted that the process of the invention is not merely a physical process of extraction but incorporates chemical changes. These inventors observe that hydrolysis and esterification reactions occur during the process of extraction resulting in the release of said aglycons in the extract. This hypothesis is submitted without commitment, as the higher medicinal efficacy stands established by the experimental investigations of the inventors. This invention has experimental proof that chemical reactions are occurring during extraction so that the extraction process of the invention involves a combination of physical and chemical changes. This invention prepared a hexane extract and also an extract wherein the first solvent was ethanol and the second was hexane. The yield in the former procedure was found to contain about 35% more LCs. HPLC analysis indicates the presence of aglycons, steroidal terpenes and long chain fatty acids structures in the extract. It is inferred that the extra yield corresponds to the existence of these aglycons, steroidal terpenes and long chain fatty acids in the hexane extract. These compounds, which are either originally present in the S family plant matter or are reaction products involving some of said originally present compounds, are substantially absent in the extract obtained by the ethanol-hexane solvent system. The ethanol-hexane solvent system leaves out these components during extraction.

The extract of the invention further contains the fatty acids found in the S. family plants. The S. family glycosides are highly bitter compounds that make the prior art *PK* extracts unpalatable. In contrast, the *PK* extract of the invention is highly palatable being almost free of bitterness factors. A number of odour factors come out in water and alcohol extracts and consequently the prior art *PK* extracts have a strong unpleasant odour that reduces their acceptability for human and animal consumption. Said picrosides and other glycosides in the S. family are highly bitter compounds. Smaller quantities of other bitter principles are also found in *PK* plants. On the other hand, the extract of the invention is substantially odourless. All in all, the extract of the invention is a distinct and different paradigm from the prior art extracts.

The mechanism of the medicinal action of the terpenes and other components of the extract of the invention is not known nor is there an explanation of the superiority of their medicinal action vis-à-vis the prior art extract components. These inventors again observe that the said superior medicinal activity is experimentally established by their experimental work.

The drawbacks of the prior art extracts are therefore, the presence of the glycoside components that are of considerably lesser medicinal efficacy than the said terpenes and other LCs of the S. family of plants. The range of medicinal effectiveness of the glycosides is also considerably lesser than that of the said terpenes and other LCs.

Although they are reported to be hepatoprotective, the said glycosides do not possess anti-viral activity (Herbal medicines for liver diseases in India, S P Thyagaraj an, S Jayaram, V Gopalakrishnan, R Hari, P Jeyakumar, MS Sripathi, Journal of Gastroenterology and Hepatology Volume 17, pages S370-S376, December 2002). The said LCs on the other hand, exhibit strong anti-viral activity both against DNA and RNA viruses and their action is therefore much wider than the reported limited liver-protective and regenerative action of the said NLCs. The prior art extracts are highly bitter such as to be almost unpalatable and their unacceptability extends further to their strong unpleasant odour components.

The drawbacks of the prior art processes of extraction are that they are confined to water and the two alcohols, ethanol and methanol and do not extend to a whole range of solvents that yield novel and better and medicinally more useful effective extracts containing the LCs of the S. family.

These inventors have experimentally established through cell lines that the use of *PK* extracts mainly comprising said lipophillic components actively inhibits the action of hepatitic and other viruses of the DNA and RNA types. It further destructs the viral structures providing confirmation that it is a highly effective anti-viral composition.

As is known, phospholipids involved the structure of cell membranes comprise two highly lipophilic (fat-loving) alkyl chains and a highly hydrophilic (water-loving) ionic group at the other end, typified by choline phosphate. The inventors believe that this allows the lipophillic moieties and other structures in *PK* extracts to be more active pharmacologically in the treatment of viral diseases. The in vitro investigations by the present inventors have been confirmed by independent labs. They confirm that *PK* lipophillic compounds have very high anti-viral properties against DNA and RNA viruses including Hepatitis B, influenza, retroviruses such as HIV, and other viruses.

These inventors observe that a combination(mixture) of one or more of the terpenes found in the said. S. family of plants with one or more of the fatty acids found in said family of plants is a novel potent anti-viral composition that is highly effective against a number of viral, fungal, bacterial, parasitic and protozoal infections, disorders and diseases. Said novel composition is effective against both DNA and RNA viruses. In view of that it has applications in biochemical and biotechnical processes in research and industry, in particular the technical fermentation industry. The novel composition of the invention may further comprise one or more of the aglycons of the glycosides found in the said family of plants. The constituents of the composition of the invention may be of plant origin, or synthetic or part-synthetic origin. Said composition may be made by a process of admixture of said constituents or obtained partly or fully from plant matter.

This invention has extracted the said S. family plant matter in general and of the *P*. genus in particular. These extracts were fractionated by HPLC(High Performance Liquid Chromatography) to yield several fractions. It is observed that said fractions also constitute compositions of the invention as each of them comprises the said terpenes and fatty acids of the S. family plants. Said fractions are elaborated further hereinbelow.

These inventors have discovered that when a human or animal subject is administered the said extract or composition of the invention, antigens and antibodies are produced by the body's immune processes. Though the mechanism of this process is not fully known, these inventors have established that antibodies and allied species and substances such as antigens, immunogens, immune sera, anti-serum, serum, immunoglobins are produced in said subjects and can be isolated from the serum of human, animal, bird or aquatic animal subjects employed, that is, subjects that have been administered the extract or the composition of the invention. Antibodies and allied species thus isolated may be used to formulate vaccines, adjuvants and other formulations for administration to subjects who are in need of prevention or treatment. Said antibodies, allied species and substances are collectively referred to herein as 'immune system related species'.

It is therefore an object of this invention to provide a composition comprising a mixture of the terpenes and fatty acids found in the plant matter of the Scrophulariaceae family(order) of plants.

It is a further object of this invention to provide a *PK* extract that is lipophillic and wherein the lipophillic components of *PK* plant matter are substantially the major components thereof and are preferably said terpenes and fatty acids.

It is a still further object of this invention to provide a *PK* extract wherein substantially all the lipophillic components of *PK* are faithfully represented in the extract.

It is a still further object of the invention to provide a *PK* extract wherein the non-lipophillic components of *PK* are substantially absent or are minimised.

It is a still further object of this invention to provide a *PK* extract wherein the bitter principles, in particular the *PK* glycosides and the unpleasant odour components present in *PK* are substantially absent or are minimised.

It is a still further object of the invention to provide for a process of extraction for making a *PK* extract wherein said lipophillic factors are the major components and wherein the non-lipophillic factors of *PK* are substantially absent or minimised.

It is a still further object of this invention to provide for a said extraction process such that the full set of lipophillic factors originally present in the *PK* plant matter are faithfully brought out in the extract and that said hydrolysis and esterification reactions are allowed to proceed and indeed encouraged.

It is a still further object of this invention to provide a process of extraction for making a *PK* extract wherein the extraction of the terpenes and the fatty acids in the original plant matter is maximised and further the maximum conversion of the glycosides to aglycons and subsequent extraction thereof is achieved by the suitable selection of solvents and the choice of extraction parameters.

It is a still further object of this invention to provide a set of solvents whereby *PK* extraction can be carried out to obtain an extract, the major components whereof are said lipophillic compounds and that substantially prevent, or minimise the extracting out of the non-lipophillic constituents and/or the bitter and the unpleasant odour components thereof originally present in the *PK* plant matter being extracted.

It is a still further object of this invention to obtain said immune system related species by administering the composition of the invention to human, animal, bird, aquatic animal and other subjects, and to devise a process for the same.

According to the invention, therefore, there is provided a medicinal, nutraceutical or food composition for use in the prevention, elimination, treatment and management of viral, fungal, bacterial, parasitic and protozoal infections, disorders and diseases in human and animal subjects and for use in other applications as hepatoprotective, anti-hyperlipidemic anti-diabetic and kidney protective agents, comprising one or more of the terpenes found in the Scrophulariaceae family of plants and one or more of the fatty acids found in the said family.

According to the invention, therefore, there is further provided a method of treatment, for the prevention, elimination, treatment and management of viral, fungal, bacterial, parasite and protozoal infections, disorders and diseases in human and animal subjects; and in the pharmaceutical, biochemical, biotechnical and fermentation research and industry, by the administration to the subject of an adequate dose of a composition comprising one or more of the terpenes found in the Scrophulariaceae family of plants and one or more of the fatty acids found in said family, over an adequate period of time optionally followed by suitable maintenance doses of said composition over an adequate period of time.

According to the invention, therefore, there is further provided a process for making a medicinal, nutraceutical and food composition for use in the prevention, elimination, treatment and management of viral, fungal, bacterial, parasitic and protozoal infections, disorders and diseases in human and animal subjects and for use in other applications, by admixture of one or more of the terpenes found in the Scrophulariaceae family of plants with one or more of the fatty acids found in the said family.

According to the invention, therefore, there is further provided immune system related species such as lymphocytes, serum, anti-serum, plasma, antibodies, antigens, peptides, enzymes, immune sera, immunoglobulins, immunogens and adjuvants for use in the prevention, elimination and treatment of infections, disorders and diseases caused by viruses, fungi, bacteria, parasites and protozoa in humans and animals, said species being generated in human, animal, bird or aquatic animal subjects by the administration to said subjects of a composition of the invention such as to cause production of said species by the immune systems thereof, the said species being subsequently isolated and harvested for use in said prevention, elimination and treatment.

According to the invention, therefore, there is further provided a process for the production of immune system related species such as lymphocytes, serum, anti-serum, plasma, antibodies, antigens, peptides, enzymes, immune sera, immunoglobulins, immunogens and adjuvants for use in the prevention, elimination and treatment of infections, disorders and diseases caused by viruses, fungi, bacteria, parasites and protozoa in humans and animals, comprising providing a composition comprising the terpenes and the fatty acids found in the Scrophulariaceae family of plants; administering the said composition to human, animal, bird or aquatic animal subjects such as to cause the generation of said species by the immune systems thereof; harvesting and isolating said species from the sera and anti-sera thereof for use in said prevention, elimination and treatment.

According to the invention, therefore, there is further provided a process for making a medicinal, nutraceutical and food composition for use in the prevention, elimination, treatment and management of viral, fungal, bacterial, parasitic and protozoal infections, disorders and diseases in human and animal subjects and for use in other applications, by admixture of one or more of the terpenes found in the Scrophulariaceae family of plants with one or more of the fatty acids found in the said family.

The composition of the invention and the PK extract of the invention therefore essentially comprise the terpene constituents of the S. family of plants. In the description further hereinbelow, references to the composition of the invention may also be considered to be references to the extract of the invention and vice versa unless repugnant to the context. They may comprise one said terpene or any mixture of the terpenes of the S. family. They further essentially comprise one or more of the fatty acid(s) of the S. family of plants. The combination of said terpenes and fatty acids exhibits therapeutic synergy. Such synergy is also exhibited by the three component system: said terpenes, fatty acids and aglycons. Preferably, the terpenes are the single major LC component and the terpenes and fatty acids together form the major part of the said lipophillic components in the composition/extract. Said extract and composition also preferably comprise the aglycons of the glycosides present in the S. family plants. These glycosides undergo reactions (like hydrolysis) and/or decomposition under the extraction conditions and yield their respective aglycons that are then extracted out by the solvents of the invention into the extract. Preferably, the combined amount of the said terpenes, fatty acids and the aglycons, that is of the LCs as a whole is 80% by wt or more. Preferably, the extract of the invention is free of the said bitter glycosides and the amount of the other NLCs in the extract is between. 0.01% by wt. and 20% by wt of the extract as a whole. Preferably, the amount of said glycosides, kutkisides, picrosides and apocynin and drosin together does not exceed 20% by wt of the extract. Preferably less than 10% of the extract is water-soluble. The parameters given hereinabove are applicable to both said composition and extract of the invention unless otherwise required by the context.

Within the scope of the invention said constituents of the composition of the invention may be of partly or fully of plant origin or of synthetic or other origin or combinations thereof. The composition of the invention may comprise substantially only the said terpenes and fatty acids but may additionally comprise fillers and other neutral material. Aside the said essential terpenes and the fatty acids, said composition may comprise additional therapeutic, nutritional, food or other factors or factors to modify the taste, colour, texture, flavour, bulk and others and provide additional therapeutic action. Said composition may contain any of the other constituents of the S. family of plants within the scope of the invention.

A plant extract such as of one or more members of the S. family of plants that comprises inter alia said essential constituents of the composition of the invention constitutes the composition of the invention.

Within the scope of the invention, the said PK extract of the invention may be the extract of any species in said S. family of plants. It will be noted that the process of extraction of the invention is easily and simply extensible to any said plant species or other plant matter. Equally easily and simply the said process is adaptable to any mixture of said species. Preferably, the extract is from a mixture of the three species mentioned hereinabove: *Picrorhiza kurrooa* Royle, *Picrorhiza scrophulariflora* Pennell and *Neopicrorhiza scrophulariiflora*. These three species are favoured from the point of view of toxicity.

Within the scope of the invention, the said extract of the invention may be derived partly or fully from any other plant matter that comprises the said terpenes, fatty acids and the glycosides or similar constituents of the said S. family. It will be noted that the process of extraction of the invention is easily and simply extensible to plant species other than that of said S. family or to mixtures of plant species.

The plant matter used for extraction may be any part of the plant such as the roots, rhizomes, stem, leaves, flowers, bark, seeds and others. Within the scope of the invention, any mixture or combination of said parts may be extracted. Preferably, the plant matter extracted is either the roots or the rhizomes, more preferably a mixture of the two. Any other mixture of said parts is also within the scope of the invention.

The extraction process of the invention is a solid-liquid extraction process. As mentioned hereinabove, the plant matter may be any plant of the S. family of plants. Within the scope of the invention, it can be a mixture of plant matter from different said plants.

Preferably, the plant matter is from the species *Picrorhiza kurrooa* Royle or from *Picrorhiza scrophulariflora* Pennell or *Neopicrorhiza scrophulariiflora* or any mixture or combination of the three species.

The said preparatory steps are optional and one or more thereof may be adopted as required. Extraction can be carried out on wet or dry plant matter. Preferably, the matter is pre-dried either by solar drying or process drying. Preferably the plant matter is cut and chopped to reduce the size to ensure better solid-liquid contact in the extraction step. Preferably, the plant matter is crushed and ground to a size range of about 1-5 mm size or below. Preferably a blanching operation is carried out.

Extraction can be single-stage or multi-stage, within the scope of the invention. If the latter, the different plant materials and extract (solution streams) may be combined or disposed in different arrangements to give counter-currents, co-currents, series, parallel and hybrid combinations. These observations also apply for the mixing and combinations of said extracts/solutions for further processing operations.

The solvent adopted in the process of the invention is non-aqueous. It is preferably non-polar, but polar and other solvents are within the scope of the invention. Preferably it is non-alcoholic but monohydric alcohols of chain length of four or more C-atoms may be used even though they are polar. The solvent preferably either has a hydrocarbon chain of four or more C-atoms in its structure or a cyclic or ring portion therein. Without limitation to the scope of the invention the solvent may be one from, but not limited to, the following list Dichloromethane, hexane, n-hexane, c-hexane, toluene, t-BuOMe, Et2O, Methyl Iso Butyl Ketone, Vinylacetate, ethyl acetate, t-butanol, DMA, i-propanol, formic acid, formamide, methyl ethyl ketone, N,N-dimethylformamide, acetic acid, acetone, acetonitrile, benzene, 1-butanol, 2-butanol, 2-butanone, 1-butyl alcohol, carbon tetrachloride, chlorobenzene, chloroform, cyclohexame, 1,2-dichloroethane, diethyl ether, diethylene glycol, diglyme(diethylene glycol dimethyl ether), 1,2-dimethoxy-ethane(glyme, DME), dimethylether, dimethyl-formamide(DMF), dimethyl sulphoxide(DMSO), dioxane, ethanol, ethyl acetate, ethylene glycol, glycerine, heptane, hexamethylphosphoramide(HMPA), hexamethylphosphorous triamide(HMPT), methanol, methyl t-butyl ether(MTBE), methylene chloride, N-methyl-2-pyrrolidinone(NMP), nitromethane, pentane, petroleum ether, ligroine, 1-propanol, 2-propanol, pyridine, tetrahydrofuran(THF), triethyl amine, o-, m- and p-xylenes, white spirit, vegetable oils, petroleum naphtha, turpentine, oxygenated solvents(like alcohols, glycol ethers, methyl acetate, ethyl acetate, ketones, esters, glycol ether, glycol esters); organic compounds used as solvents include aromatic compounds and other hydrocarbons, alcohols, esters, ethers, ketones, amines, and nitrated and halogenated hydrocarbons, inorganic solvents like ammonia, sulphuric acid, sulphuryl chloride fluoride, surfactants, detergents, pH buffers, water and heavy water.

Within the scope of the invention the extraction may be carried out with a solvent mixture of any two or more of the above solvents. Alternatively, within the scope of the invention, extraction may be carried out in series employing two or more solvents selected from the above. Alternatively, the extraction may be by a series of solvents or by a solvent mixture.

The process of extraction of the invention comprises a solid-liquid extraction step wherein the plant matter is contacted with a suitable solvent(s). The extract of the invention may be produced by the process of the invention or other within the scope of the invention. Within the scope of the invention, the extract of the invention may be prepared by any of the known means for carrying out the extraction step such as: solvent extraction, absorbent gel extraction, liquefied gas(like CO2) extraction, enzymatic process, membrane filtration, liquid-liquid extraction, liquid-solid extraction, resin extraction, reverse phase extraction, chromatography or others.

Within the scope of the invention, the extract product of the invention after removal of the solvent by evaporation or other means may be dried or subjected to other operations such as grinding, screening, milling, mixing, granulating, adsorbing on excipients or others. The extract may be in the form of nanoparticles, nano gels or processed to constitute a vaccine or an adjuvant.

Within the scope of the invention, the extract of the invention may further contain one or more of the following constituents of the said S. family of plants or other plants: glycoside esters, glycoside ethers, aliphatic compounds, aromatic compounds, glycosidic carboxylates, steroidal glycosides, long chain fatty acids, aglycones, acylated aglycons, fatty alcohols, fatty acids, steroidal esters, steroidal fatty acids, steroidal alcohols, sterols, terpenoids, steroidal triterpenes, oxidised triterpenes, esters of triterpenes, acids of triterpenes, alcohols of triterpenes, cucurbitacins, terpenoid moieties having 5-40 C-atoms, long-chain hydroxyl fatty acid moieties, resin acids, triterpenoids built on steroidal skeleton.

Within the scope of the invention, the extract may be in any of the known forms for administration by oral, intravenous, intramuscular, sub-cutaneous, peritoneal, rectal, nasal, trans-dermal, dermal, sublingual, vaginal or other routes. It may also be in the form of any of the known medicinal salts and may comprise additives for colour, flavour, taste, texture, bulk and others. The extract of the invention may also contain additional therapeutic factors as added additives that provide either additional efficacy or combination therapeutic effect or both. Said additives may be nutrition factors to yield a nutraceutical or food composition with therapeutic action. Examples of such additives are: sugars, vitamins, minerals, amino acids, metals, oils, fatty acids, alcohols, solvents and other plant extracts. The extract of the invention may be a solid form composition or a solution of said lipophillic components in a suitable base or adsorbed on any of the known excipients. The extract of the invention may be optionally processed further to modify its properties, form, shape, colour, texture and it increase its effectiveness and acceptability. Any such modified forms of the said extract are within the scope of the invention. Examples of such modifying processes are: Standardization of extract, fractionation to obtain different fractions, homogenisation, fortification, enzymatic process to increase the absorption and others. As mentioned, observations with regard to the extract are applicable also to the composition of the invention unless the context requires it to be otherwise.

The extract of the invention may be in the form of a fraction within the scope of the invention. The extract may be fractionated by any of the known means such as HPLC-High Performance Liquid Chromatography, Gas Chromatography(GC) or others. Within the scope of the invention, any of said fractions or mixtures thereof may constitute the extract of the invention.

The inventors have carried out fractionation by the HPLC procedure and subjected the fractions to NMR analysis.

Preferably, the solvent adopted in the extraction process of the invention is a non-polar hydrocarbon solvent. More preferably, the solvent is n-hexane. The invention has investigated the use of the composition and extract of the invention in the following applications:

1. as an hepatoprotective agent and against any hepatitis virus and toxin,
2. as a anti-hyper-lipidemic, anti-diabetic and kidney protective agent;
3. against bacterial infections in biochemical, pharmaceutical and biotech processes in research and industry;
4. to establish efficacy against any RNA virus in particular the influenza viruses and retroviruses;
5. to establish efficacy against DNA virus in particular the herpes virus of the order Herpesviridae;
6. as a prophylactic in respect of liver ailments and toxins and ailments of other organs;
7. as a prophylactic against viruses in general;
8. in general against any virus, bacteria, fungus or protozoa;

9. as a vaccine and an adjuvant to vaccines; and
10. against any infection, disorder and disease caused by any of the agents mentioned.

The range of the dosage worked out by these inventors in respect of the abovementioned applications is from about 1 mg per dose to about 1000 mg. per dose where the weight refers to the combined amounts of said terpenes and fatty acids therein.

In order to provide a clearer understanding of the invention some of the embodiments thereof are described hereinbelow without limitation to the scope of the invention.

Embodiment 1

1. Roots and rhizomes of said *PK* plants were procured and sun-dried. Manual picking of foreign particles was carried out.
2. The plant matter was subjected to water washing by means of sprinklers to remove sand and dirt.
3. The plant matter was then air dried under vacuum to bring down the moisture.
4. The plant matter was then ground manually and the ground matter air dried to remove traces of moisture.
5. A batch of this matter was weighed and charged into the reactor (extraction vessel).
6. Hexane was added and the solid-liquid mixture heated. (Alternative any other non-polar solvent).
7. The heated mixture was continuously stirred.
8. The extraction process including the said reactions was allowed to proceed for a period of about 24 hours.
9. The plant matter and the solution were separated.
10. The solution was transferred to another vessel under vacuum.
11. The solution was filtered thrice to remove suspended matter and undissolved matter and thereafter the solution was sent to a reaction vessel (evaporator) where the solvent was evaporated under vacuum. The temperature was maintained at below 70C. during evaporation.
12. The solvent was recovered and sent for re-use in the extraction.
13. The solid residue resulting from evaporation was air dried under vacuum in a controlled atmosphere. The dried material is the extract product of the invention and the same was sent for testing.

Embodiment 2

1. Steps 1 and 2 as in embodiment 1.
2. The *PK* plant matter was ground into small pieces by mechanical means.
3. A batch was measured out and loaded into the reactor (extraction vessel).
4. A mixture of solvents, pentane and ethyl acetate was charged to the reactor. (Alternatives: Any mixture of pentane, ethyl acetate, acetone, n-hexane, ether, chloroform and tetrahydrofuran).
5. Reactor contents heated and stirred continuously. Extraction carried out for about 36 hours.
6. Separation of the plant matter and solution carried out,
7. The solution was transferred to another vessel under vacuum.
8. The solution was filtered thrice and the clear liquid was evaporated at about 80C under vacuum.
9. Solvent recovered.
10. The solid residue from the evaporation collected and subjected to air drying under vacuum in an atmosphere of nitrogen (alternatively carbon dioxide).
11. The dried product is the product extract of the invention. It was sent for testing.

Embodiment 3

1. Same steps as 1 and 2 of embodiment 1.
2. The *PK* plant matter was mashed into a paste and mixed with sufficient quantity of water.
3. Organic acid (alternatively an inorganic acid) was added to bring down the pH so as to initiate the esterification reaction of the glycosides.
4. Stirring continued for about 24 hours.
5. At this stage, the n-hexane solvent was added (alternatively petroleum ether) and extraction continued for about 4 hours with stirring.
6. The solution was decanted and filtered.
7. The solvent was evaporated from the solution under vacuum by heating at about 75C.
8. The semi-solid residue was collected and lypolised at about minus 80C. under vacuum and further process to obtain it in a powdered form.
9. The powder is the extract product of the invention and was sent for testing.

Embodiment 4

1. Same as steps 1 and 2 of embodiment 1.
2. The *PK* plant matter is ground into a paste and steam distilled.
3. The steam is condensed and the residual solution after steam distillation is collected.
4. Enzyme esterase is added. pH and temperature are adjusted and the solution stirred for about 6 hours.
5. The temperature was raised to about 100C. to under vacuum to denature the enzyme.
6. The solution was then cooled.
7. Petroleum ether was added and the mixture stirred for about 4 hours.
8. The solution was filtered to remove the enzyme debris and un-dissolved particles.
9. The solution was separated into a petroleum ether layer and an aqueous layer.
10. The petroleum ether was heated to evaporate the solvent under vacuum,
11. The solid residue was collected being the extract product of the invention.
12. The extract product was air dried and sent for testing.
13. The water was evaporated from the aqueous layer. The evaporation was under vacuum. The residue contains the water soluble components in the *PK* plant matter.

Embodiment 5

1. Same as steps 1, 2 and 3 of embodiment 1.
2. The *PK* plant matter is ground into small pieces by mechanical means.
3. A batch is measured out and loaded into the extractor reactor.
4. A measured quantity of solvent ethanol(alternative: methanol) charged to the reactor.
5. Reactor contents heated to the required level while stirring and maintained at those conditions for about 24 hours.

6. The solution is transferred to another reactor vessel under vacuum.
7. The solution was filtered three times.
8. Water is added to the solution and stirred for about 1 hour.
9. Solvent n-hexane(alternatively pentane) added and the contents stirred for about 6 hours.
10. The solution is allowed to settle for about 4 hours.
11. Evaporation under vacuum carried out to distil off the solvent to recover the extract product of the invention in a solid or semi-solid form.
12. Balance liquid containing water and alcohol is distilled to recover the solvent.
13. Product air dried under vacuum in nitrogen atmosphere (alternatively CO2 atmosphere) and sent for testing and microbial examination.

Embodiment 6

1. Steps 1 to 3 same as in embodiment 1.
2. Same as item 2 in embodiment 5.
3. A batch of the *PK* plant matter is measured out and loaded into the extractor reactor.
4. The reactor is charged with the required quantity of n-hexane (alternative solvents for this embodiment: pentane, 1,4-di-oxane, di-ethyl ether and petroleum ether.
5. The reactor contents are heated to the required level and stirred for about 24 hours.
6. The solution transferred to another vessel under vacuum and filtered three times.
7. The solution heated to evaporate the solvent under vacuum to obtain the extract product of the invention in solid or semi-solid form.
8. Residual solvent removed from product by air drying under vacuum in a nitrogen atmosphere(alternatively a CO2 atmosphere).
9. Product sent for testing for physical properties and microbial evaluation.

Embodiments and variations other than described herein above are feasible by persons skilled in the art and the same are within the scope and spirit of this invention.

REFERENCES

1. Kamble, et al., Hepatoprotective activity studies of herbal formulations, International Journal of Green Pharmacy, July-September 2008
2. *Picrorhiza kurroa*—evaluation of therapeutic properties, Alternative Medicine Review, 2001
3. A. Russo et al., Indian medicinal plants as antiradicals and DNA cleavage protectors, Phytomedicine, Vol. 8(2), pp. 125-132, 2001
4. Anamika Khajuria, et al., RLJ-NE-299A: A new plant based vaccine adjuvant, Vaccine 25 (2007) 2706-2715
5. Pandey B L and Das P K, Indian journal of physiology and pharmacology 32(2):120-5, 1988
6. Vaidya A B, et al., Picrorhiza kurroa (Kutaki) Royle ex Benth as a hepatoprotective Agent—experimental & clinical studies, Journal of Postgraduate Medicine, Vol.42, Issue.4, pages 105-8, Year 1996.
7. http://wvvw.thorne.com/media/picrorhiza_monograph.pdf - - - monograph.
8. Herbal medicines for liver diseases in India, S P Thyagarajan, S Jayaram, V Gopalakrishnan, R Hari, P Jeyakumar, M S Sripathi, Journal of Gastroenterology and Hepatology Volume 17, pages S370-S376, December 2002

We claim:

1. A medicinal, nutraceutical or food composition for use in the treatment or management of viral, fungal, bacterial, parasitic and protozoal infections, disorders and diseases in human and animal subjects and for use as hepatoprotective, anti-hyper-lipidemic, anti-diabetic, kidney-protective, and immunomodulation agents, the composition comprising:
   one or more terpenes, and one or more fatty acids, wherein the one or more terpenes and the one or more fatty acids include terpenes and fatty acids collected during a non-aqueous extraction of a plant matter from one or more plants selected from the group consisting of *Picrorhiza kurroa, Neopicrorhiza scrophulariiflora*, and *Picrorhiza scrophulariiflora* Pennell, and
   the composition being substantially free of picrosides, other glycosides, and apocynin,
   wherein the composition comprises at least 20% by wt. of lipophillic components, and wherein an amount of the one or more terpenes and the one or more fatty acids together being more than about 50% by wt. of a total weight of the lipophillic components in the composition.

2. The composition as claimed in claim 1 further comprising one or more of the other lipophillic constituents found in the said one or more plants.

3. The composition as claimed in claim 2, wherein said one or more of the other lipophillic constituents comprises one or more of the aglycons of the glycosides found in the said one or more plants.

4. The composition as claimed in claim 1, wherein the composition comprises no more than about 20% by wt. of non-lipophillic components.

5. The composition as claimed in claim 1, wherein the amount of water-soluble components in the composition do not exceed about 10% by wt. of the amount of said lipophillic components in the composition.

6. The composition as claimed in claim 1, wherein the amount of bitter and odor components in the composition are not more than about 0.5% by wt.

7. The composition as claimed in claim 1, further comprising one or more additional components that provide complementary or supplementary therapeutic efficacy and/or are additional factors for nutrition, food, color, taste, texture, odor, flavor, bulk and other characteristics.

8. The composition as claimed in claim 1, the composition being in a form suitable for administration through oral, intravenous, intramuscular, sub-cutaneous, peritoneal, rectal, nasal, trans-dermal, dermal, sublingual, vaginal or other routes.

9. The composition as claimed in claim 1, wherein the medicinally active components in the composition are in the form of any of the medicinally accepted salts.

10. The composition as claimed in claim 1, the composition being in a form selected from the group consisting of a powder, syrup, drink, tablet, caplet, softgel, capsule, nanogel, nano-particles, injections, parenteral, transdermal patches, absorbent gels, nasal sprays, vaginal gel, and adsorbed on an excipient.

11. The composition as claimed in claim 1, wherein one or more of the constituents of the composition are partly or fully derived from plant matter.

12. The composition as claimed in claim 1, wherein the plant parts wherefrom said constituents are derived are selected from the group consisting of leaves, stems, rhizomes, roots, flowers, bark, seeds, and mixtures thereof, of the plants.

13. The composition as claimed in claim 1, further comprising one or more other compounds found in, or derived from, the constituents of the said plants and is selected from the group consisting of glycoside esters, glycoside ethers, aliphatic compounds, aromatic compounds, glycosidic carboxylates, steroidal glycosides, long chain fatty acids, aglycones, acylated glycodes, fatty alcohols, fatty acids, steroidal esters, steroidal fatty acids, steroidal alcohols, sterols, terpenoids, steroidal triterpenes, oxidised triterpenes, esters of triterpenes, acids of triterpenes, alcohols of triterpenes, cucurbitacins, terpenoid moieties having 5-40 C-atoms, terpenes and their fatty acids, esters, sterols, steroids, alcohols, salts, carbohydrates, acids, saponins, alkaloids, phenols, tannins, lignins, flavonoids, hormones, pigments, catechin, proteins, peptides, oxidized forms, hydrocarbons, long-chain hydroxyl fatty acid moieties, resin acids, and triterpenoids built on steroidal skeletons.

14. The composition as claimed in claim 1, wherein a content of said composition that is partly or fully derived from plant matter comprises one or more fractions, or mixtures thereof, obtained by fractionation of the extract obtained by extraction of said plant matter.

15. The composition as claimed in claim 1, wherein the non-aqueous extraction is conducted using a solvent, solvent mixture or solvent series selected from the group consisting of dichloromethane, hexane, n-hexane, c-hexane, toluene, t-BuOMe, Et20, methyl iso Butyl ketone, vinylacetate, ethyl acetate, t-butanol, DMA,i-propanol, formic acid, formamide, methyl ethyl ketone, N,N-dimethylformamide, acetic acid, acetone, acetonitrile, benzene, 1-butanol, 2-butanol, 2-butanone, 1-butyl alcohol, carbon tetrachloride, chlorobenzene, chloroform, cyclohexane, 1,2-dichloroethane, diethyl ether, diethylene glycol, diglyme(diethylene glycol dimethyl ether), 1,2-dimethoxy-ethane(glyme, DME), dimethylether, dimethyl-formamide(DMF), dimethyl sulphoxide(DMSO), dioxane, ethanol, ethyl acetate, ethylene glycol, glycerine, heptane, hexamethylphosphoramide(HMPA), hexamethylphosphorous triamide(HMPT), methanol, methyl t-butyl ether(MTBE), methylene chloride, N-methyl-2-pyrrolidinone(NMP), nitromethane, pentane, petroleum ether, ligroine, 1-propanol, 2-propanol, pyridine, tetrahydrofuran(THF), triethyl amine, o-xylenes, m-xylenes, p-xylenes, white spirit, vegetable oils, petroleum naphtha, turpentine, oxygenated solvents, organic compounds used as solvents, and inorganic solvents.

16. The composition as claimed in claim 1, wherein the non-aqueous extraction is conducted using n-hexane.

17. The composition as claimed in claim 1, wherein the composition is in the form of a vaccine or adjuvant to a vaccine.

18. The composition as claimed in claim 1, wherein the terpenes also includes steroidal triperpenes, its esters, fatty acids, fatty acid esters, and the fatty acids also includes long chain fatty acids.

19. The composition as claimed in claim 1, wherein the non-aqueous extraction is performed with a solvent selected from hexane, liquid carbon dioxide, and petroleum ether.

20. The composition as claimed in claim 1, wherein the infections, disorders or diseases are caused by DNA viruses.

21. The composition as claimed in claim 1, wherein the infections, disorders or diseases are caused by RNA viruses.

22. The composition as claimed in claim 1, wherein the infections, disorders or diseases are selected from the group consisting of herpes, hepatitis virus, influenza, oropharyngeal candidiasis, zygomycosis, sporotrichosis, mycobacterium tuberculosis, streptococcus pneumoniae, enterohemorrahagic *E. coli* (EHEC), plasmodium parasite, HIV, and cancer causing retroviruses.

23. The composition as claimed in claim 1, wherein the composition contains the one or more terpenes and the one or more fatty acids in an amount in the range of from about 10 mg to about 1000 mg.

24. The composition as claimed in claim 1, wherein the subject is an animal.

25. The composition as claimed in claim 1, wherein the composition is administered during a biotech process.

26. The composition as claimed in claim 25, wherein the composition is administered to microorganisms.

27. The composition as claimed in claim 1, wherein the composition is in the form of a food/dietary supplement, a medicine, or an alternative medicine with or without added adjuvants.

28. The composition as claimed in claim 1, wherein the subject is a human.

* * * * *